US010786243B2

(12) United States Patent
Bunge

(10) Patent No.: US 10,786,243 B2
(45) Date of Patent: Sep. 29, 2020

(54) LOCKING SUTURE

(71) Applicant: Kent Island Holdings LLC, Greenland, NH (US)

(72) Inventor: Frederick Arnold Bunge, Sylvania, OH (US)

(73) Assignee: Kent Island Holdings LLC, Greenland, NH (US)

(*) Notice: Subject to any disclaimer, the term of this patent is extended or adjusted under 35 U.S.C. 154(b) by 9 days.

(21) Appl. No.: 14/194,309

(22) Filed: Feb. 28, 2014

(65) Prior Publication Data
US 2014/0249576 A1    Sep. 4, 2014

Related U.S. Application Data

(60) Provisional application No. 61/771,433, filed on Mar. 1, 2013.

(51) Int. Cl.
  *A61B 17/04* (2006.01)
  *A61B 17/062* (2006.01)
  *A61B 17/06* (2006.01)

(52) U.S. Cl.
  CPC ...... *A61B 17/0482* (2013.01); *A61B 17/0483* (2013.01); *A61B 17/0487* (2013.01);
  (Continued)

(58) Field of Classification Search
  CPC .................. A61B 17/06; A61B 17/062; A61B 2017/06166; A61B 2017/06176;
  (Continued)

(56) References Cited

U.S. PATENT DOCUMENTS 4,069,825 A * 1/1978 Akiyama ........... A61B 17/0467
                                              606/138
4,950,285 A * 8/1990 Wilk ...................... A61B 17/06
                                              24/16 PB
(Continued)

FOREIGN PATENT DOCUMENTS

WO    2012121538 A2    9/2012

OTHER PUBLICATIONS

Woven. (n.d.) American Heritage Dictionary of the English Language, Fifth Edition. (2011). Retrieved May 2, 2016 from http://www.thefreedictionary.com/woven.*
(Continued)

*Primary Examiner* — Kathleen S Holwerda
*Assistant Examiner* — Kankindi Rwego
(74) *Attorney, Agent, or Firm* — Loginov & Associates, PLLC; William A. Loginov

(57) ABSTRACT

This invention provides a suture system and method that does not require knots. A locking suture includes a needle and a thread that is provided with a plurality of locking barbs. The needle is applied over an end of the thread by conventional systems. The exterior surface of the thread is covered with barbs. The barbs can be arranged in rows of at least one barb each, circumscribing the thread of the suture and are oriented so that they are uniformly feathered, being closed in the direction of the needle and open toward the terminal (posterior) end. The feathering provides for the barbs to lie flat when drawn through a membrane or other material, and the bias causes them to splay open when a tension towards the terminal/posterior end is exerted. This splaying creates a locking force.

7 Claims, 11 Drawing Sheets

(52) U.S. Cl.
CPC ............ *A61B 17/062* (2013.01); *A61B 17/06* (2013.01); *A61B 2017/0496* (2013.01); *A61B 2017/06176* (2013.01)

(58) Field of Classification Search
CPC ...... A61B 2017/06185; A61B 17/0482; A61B 17/0483; A61B 17/0487; A61B 17/04; A61B 17/0469; A61B 17/0485; A61B 17/06166; A61B 17/08; A61B 17/12; A61B 17/12009; A61B 17/12013; A61B 2017/00663; A61B 2017/00654; A61B 2017/00659; A61B 2017/0488; A61B 2017/049; A61B 2017/0496; A61B 2017/06171; A61B 2017/0618; A61B 2017/0619; A61F 6/20; A61L 17/06
USPC ................ 606/228, 229, 230, 231, 144, 148
See application file for complete search history.

(56) References Cited

U.S. PATENT DOCUMENTS

| | | | |
|---|---|---|---|
| 5,053,047 A * | 10/1991 | Yoon | A61B 17/0469 606/223 |
| 5,456,722 A | 10/1995 | McLeod et al. | |
| 5,540,703 A | 7/1996 | Barker, Jr. et al. | |
| 5,683,417 A | 11/1997 | Cooper | |
| 7,285,124 B2 | 10/2007 | Foerster | |
| 7,862,584 B2 | 1/2011 | Lyons et al. | |
| 7,905,903 B2 | 3/2011 | Stone et al. | |
| 7,959,650 B2 | 6/2011 | Kaiser et al. | |
| 2004/0162579 A1 | 8/2004 | Foerster | |
| 2007/0257395 A1* | 11/2007 | Lindh | A61B 17/06166 264/171.12 |
| 2010/0274283 A1 | 10/2010 | Kirsch et al. | |
| 2011/0046642 A1 | 2/2011 | McClurg et al. | |
| 2011/0208239 A1* | 8/2011 | Stone | A61B 17/0469 606/228 |
| 2011/0282386 A1* | 11/2011 | Friedrich | A61B 17/06166 606/228 |
| 2011/0313431 A1 | 12/2011 | Shimko et al. | |
| 2012/0143349 A1* | 6/2012 | Peterson | A61B 17/06166 623/23.72 |
| 2012/0245629 A1 | 9/2012 | Gross et al. | |
| 2012/0277770 A1* | 11/2012 | Fenton | A61B 17/06166 606/151 |
| 2013/0226232 A1* | 8/2013 | Dumanian | A61B 17/06 606/224 |

OTHER PUBLICATIONS

"Affix." Merriam-Webster.com. Merriam-Webster, n.d. Web Mar. 18, 2018.*

* cited by examiner

LOCKING SUTURE

RELATED APPLICATIONS

This application claims the benefit of U.S. Provisional Application Ser. No. 61/771,433, filed Mar. 1, 2013, entitled LOCKING SUTURE, the entire disclosure of which is herein incorporated by reference.

FIELD OF THE INVENTION

The present invention relates to surgical suture materials, and more particularly, to a suture is self-locked.

BACKGROUND OF THE INVENTION

Ligation is a process of binding vessels (e.g., arteries, veins, fallopian tubes, testicular tubes and the like) using a suture, a mechanical clamp or another binding system. When a suture is used to perform a ligation, the surgeon secures it with a knot. The application of a ligation during endoscopic surgery or surgery in a tight area can create difficulties for the knotting procedure.

Surgical sutures consist of a needle and thread. The needles can be straight or curved. The curvature can describe up to ⅝ths of a circle. Most modern sutures are synthetic, including the absorbables polyglycolic acid, polylactic acid, and polydioxanone as well as the non-absorbables nylon, polypropylene and bio-compatible metal. Anti-microbial coatings can be provided to the thread to reduce infections. All sutures are classified as either absorbable or non-absorbable (dissolvable or non-dissolvable) depending on whether the body will naturally degrade and absorb the suture material over time.

Suture sizes are defined by the United States Pharmacopeia (U.S.P.). The thicknesses of threads can vary between 0.2 mm and 0.8 mm and the thickness varies with the material of the thread and the application.

The process of applying a ligation includes a needle driver or a clamping instrument (e.g., a hemostat) that is employing to control the movement of the suture. A second clamping device is applied to the vessel. The vessel is cut and the surgeon begins the process of wrapping the vessel with one or more wraps of the suture thread until the vessel is sufficiently bound. The surgeon then cuts off the needle and excess thread. This procedure is typically performed under cramped conditions that can make the knotting process difficult. This has resulted in a consideration of alternative ligation systems, including clips. The use of clips in place of knotted sutures is popular, but leaving a device within a body, even a dissolvable device, can cause secondary issues, such as infections, and other complications. It would be desirable to provide a system for a suture that does not require (can be free of) knotting and is readily used in tight situations where forming a knot is difficult.

SUMMARY OF THE INVENTION

This invention overcomes the disadvantages of the prior art by providing a suture system and method that does can be secured in a manner that is free of knots. A locking suture includes a needle and a thread that is provided with a plurality of locking barbs and a generally woven, tubular body for penetration of the needle tip therethrough. The needle is applied over an end of the thread by conventional technologies, such as adhesive, welding, crimping, and the like. The exterior surface of the thread is covered with barbs. The barbs can be arranged in rows, circumscribing the thread of the suture. The barbs are oriented so that they are uniformly feathered, being closed in the direction of the needle and open toward the terminal (posterior) end. The barbs are constructed so as to naturally be bias open in an "open" configuration when not in use and arranged to resist pull out when passed through the thread. The feathering provides for the barbs to lie flat when drawn through a membrane or other material, and the bias causes them to splay open when a tension towards the terminal/posterior end is exerted. This splaying has a locking function. The thread terminal end is optionally braided and not covered (free of) with barbs.

In use, the suture is illustratively wrapped around the vessel one or more times until the desired number of wraps is achieved. The surgeon then forces the needle through the terminal end and exerts a pulling force to draw the suture through the end until all of the slack suture thread has been passed. A reverse tension force is applied, causing a reverse pull on the thread when the pulling force is removed. This pulls against the bias of the threads, causing them to splay against the outer surface of the thread. More than one ligation can be performed with the same suture given a sufficient length of suture thread.

An illustrative locking suture system for creating a ligation comprises a suture needle and a woven thread segment having the suture needle affixed to one end and an outer surface having a plurality of barbs arranged in one or more successive circumferential rows that extend from the needle end to an unbarbed terminal end. The circumferential rows of barbs can be disposed in a regular manner at intervals of at least one barb each, the barbs constructed and arranged so as to be biased to open outwards away from the thread and aligned so that the their opening is toward the terminal end of the suture to provide fathering when drawn through the thread and to open when a tension force against the bias is exerted, thereby creating a locking structure. The barbs can be cylindrical.

An illustrative method for creating a ligation or other closure in a manner free of a knot includes the step of wrapping a vessel with successive wraps of suture. The suture needle is driven through the terminal end of the suture and the thread is drawn by a pulling force through the terminal end until the wrap is tight. The plurality of barbs lies flat during the drawing through the suture. When the pulling force is released, a reverse tension force pulls the barbs against their bias, splaying those outwards against the outer surface of the thread and thereby creating a locking structure. A second ligation can be performed using the remaining suture thread in the same manner, with the needle being driven through the thread to create the locking structure.

BRIEF DESCRIPTION OF THE DRAWINGS

The invention description below refers to the accompanying drawings, of which.

DETAILED DESCRIPTION

Figure 1:
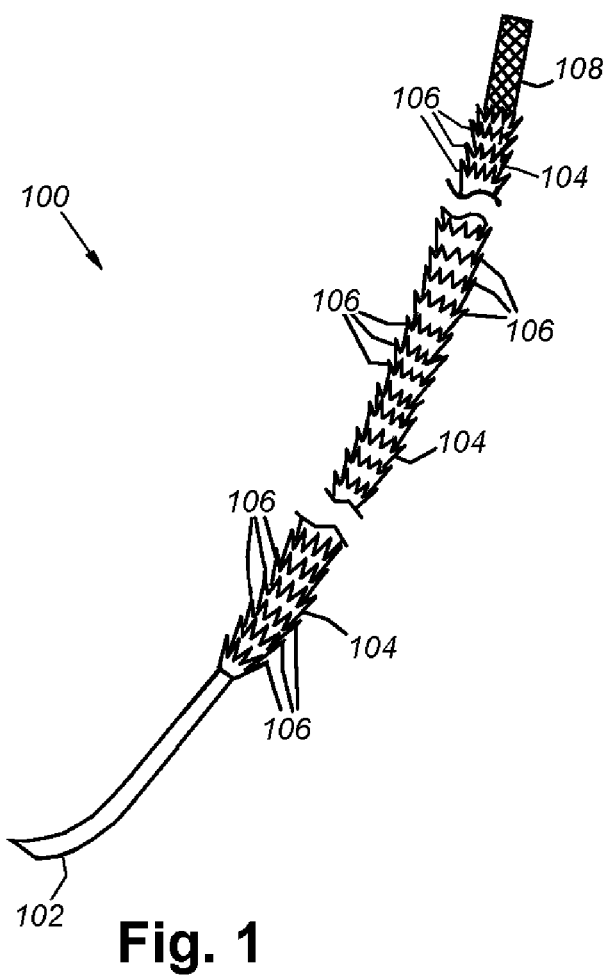
FIG. 1 is a perspective view of a locking suture according to an illustrative embodiment.

FIG. 1 depicts a locking suture 100 that is provided with a needle 102 and a woven thread 104 that is constructed and arranged with a plurality of locking barbs 106 and a braided terminal end 108. The barbs 106 are constructed and arranged to project outwardly away from the needle end and are in one or more successive circumferential rows forming the outer covering of the thread. The rows can be of a regular order, where each row of barbs 106 is aligned with the previous and following row, or an irregular order, where each row of barbs 106 is not aligned with the previous or following rows. The rows can be disposed at regular intervals. The barbs 106 are oriented so that they are uniformly feathered, being closed in the direction of the needle end and open toward the terminal (posterior) end. The barbs are constructed so as to naturally be bias open in an "open" configuration when not in use and arranged to resist pull out when passed through the thread. The feathering provides for the barbs to lie flat when drawn through a membrane or other material, and the bias causes them to splay open when a tension towards the terminal/posterior end is exerted. This splaying creates a locking force.

The underlying structure of the thread is a woven suture with two or more layers that extends from the needle 102 to the end 108. The thread 104 describes a flexible hollow tube constructed of woven threading. Conventional suture threads are non-hollow woven threads. In other embodiments, the thread is a unitary hollow tube composed of natural or synthetic polymers (e.g., polypropylene) that are dissolvable or non-dissolvable. The hollow center provides ease for passing the needle 102 through the thread. The needle tip is passed through the thread by passing through the voids between the woven warp and the weave. The structure of the weave and braided end should be sufficiently robust to enable piercing by the needle without weakening the thread's tensile strength. When tension is applied against the bias of the barbs, as will be described more fully below, the tube collapses and the threading deforms, providing a greater resistance to the barbs.

The barbs 106 can be formed by a flocking process known to those in the art, by adhering individual barb members to the woven thread. Such adhering can be accomplished by a variety of techniques, including but not limited to fusion weld, adhesives, ultra sonic welding, lamination and the like.

The needle 102 can be a conventional suture needle or a blunted tip needle for ligation. The needle can be constructed using metals (e.g., steel) or non-metals (e.g., polypropylene), or a composite thereof. The needle can be blunted for passing through the threading or a conventional needle with a sharp tip for tissue penetration.

Figure 2:
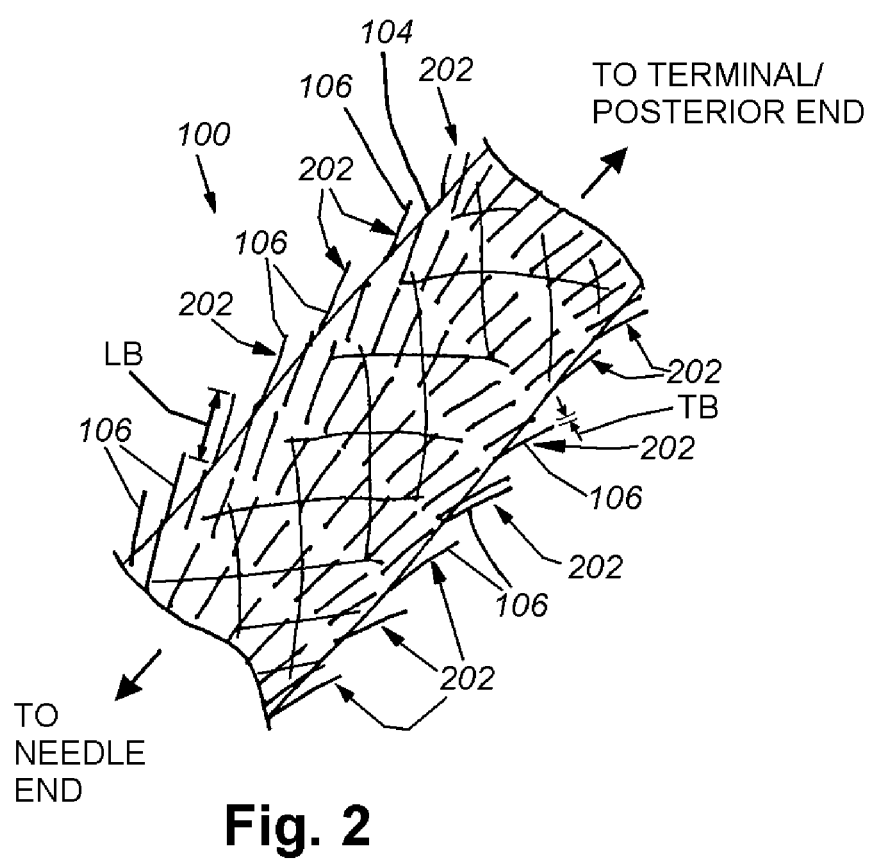
FIG. 2 is a close up perspective view of a segment of the locking suture according to the illustrative embodiment.

FIG. 2 is a close-up view of a section of the locking suture 100 and shows the barbs 106 in successive circumferential rows 202. The rows each have at least one barb 106. The thickness TB of the individual barbs 106 can vary from approximately 0.005 mm to 0.01 mm and the length LB of the individual barbs 106 can vary from approximately 0.02 mm to 0.25 mm. The size will vary according to the size of the suture and the overall purpose for the suture use.

Figure 3:
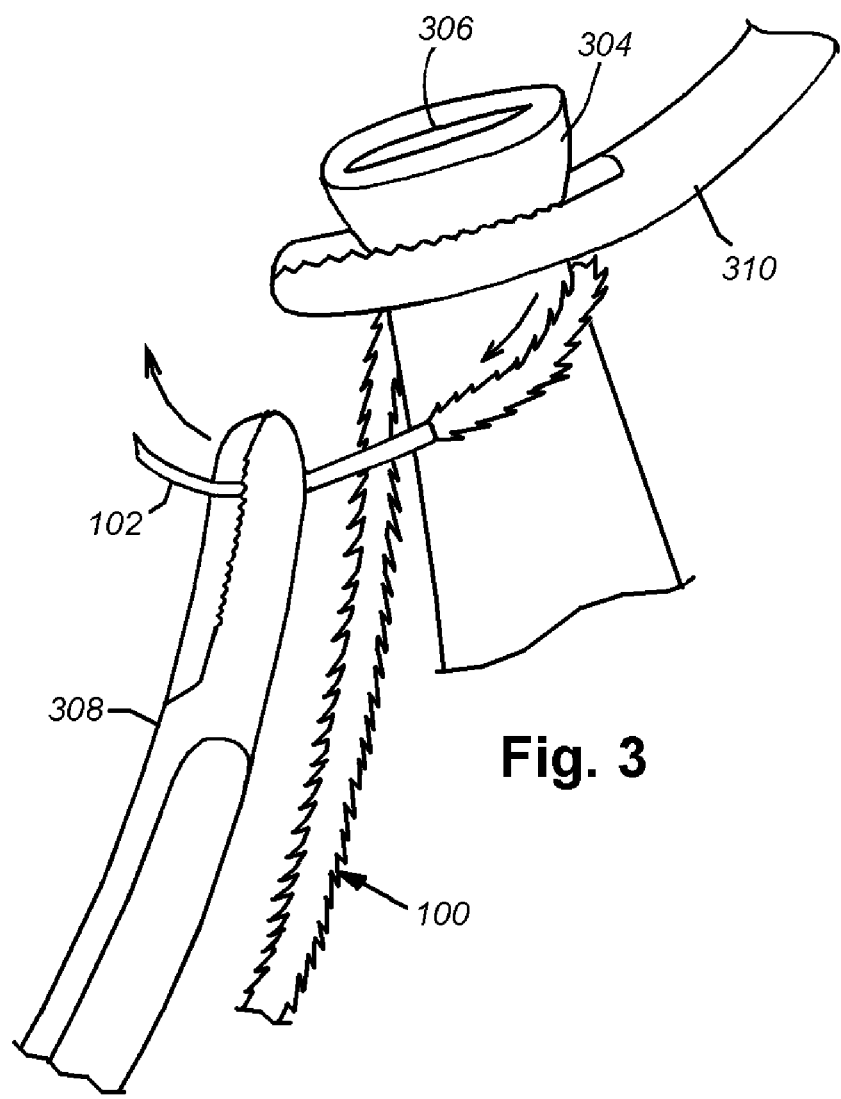
FIG. 3 is a perspective view of the locking suture being used to create a ligation according to the illustrative embodiment.

FIG. 3 is a view of a locking suture 100 in use to close a vessel 304 having an open end 306. The surgeon or other user (not shown) manipulates a hemostat 308 or other needle driver to grasp the needle end and pass the suture 100 around the vessel 304 below the opening 306 and the vessel clamp 310. This will constitute a single wrap around the vessel 304.

Figure 4:
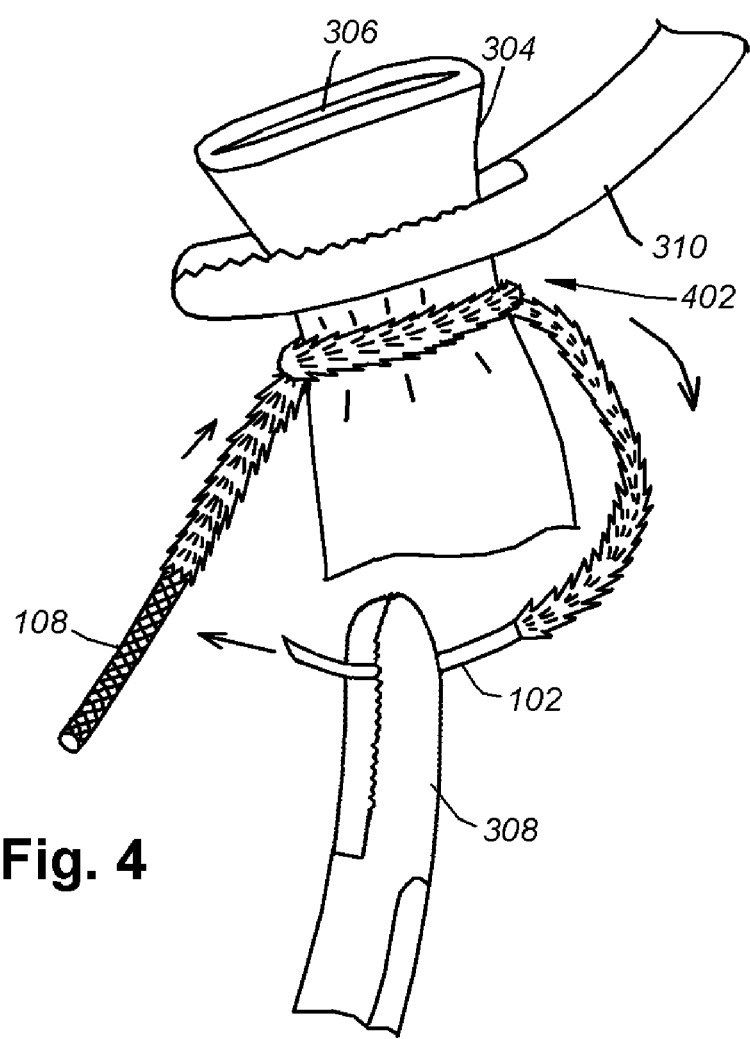
FIG. 4 is a perspective view of the locking suture looped successively around a vessel to create a ligation according to the illustrative embodiment.

FIG. 4 depicts a vessel 304 that has been wrapped by the locking suture 100 and that is now provided with a ligation of at least one wrap 402. The surgeon is about to create a lock by guiding the needle 102 through the braided terminal end 108. This lock will avoid the necessity of a conventional locking knot structure.

Figure 5:
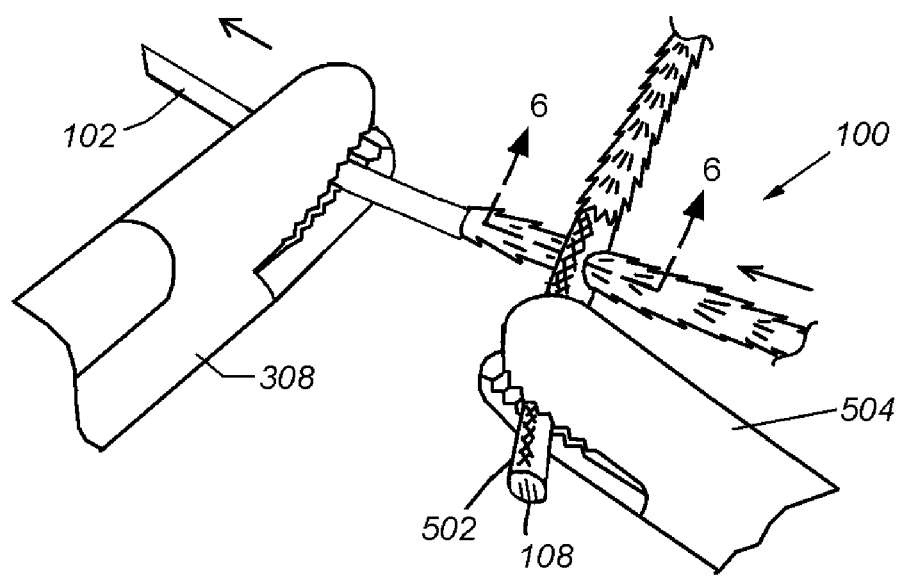
FIG. 5 is a close-up perspective view of a suture needle being driven through a terminal end of the locking suture according to the illustrative embodiment.

The surgeon controls the terminal end 108 of the suture 100 with a clamping device 504 and drives the needle 102 to pass through and/or between the threading 502 using a pulling force, as shown in FIG. 5. As noted above, the feathered bias of the barbs causes them to flatten against the thread and not resist the passage through the terminal end. The tip of the needle 102 passes through one wall of the thread, making a first path between the threading 502, through the hollow center and the second wall of the thread, making a second path between the threading.

Figure 6:
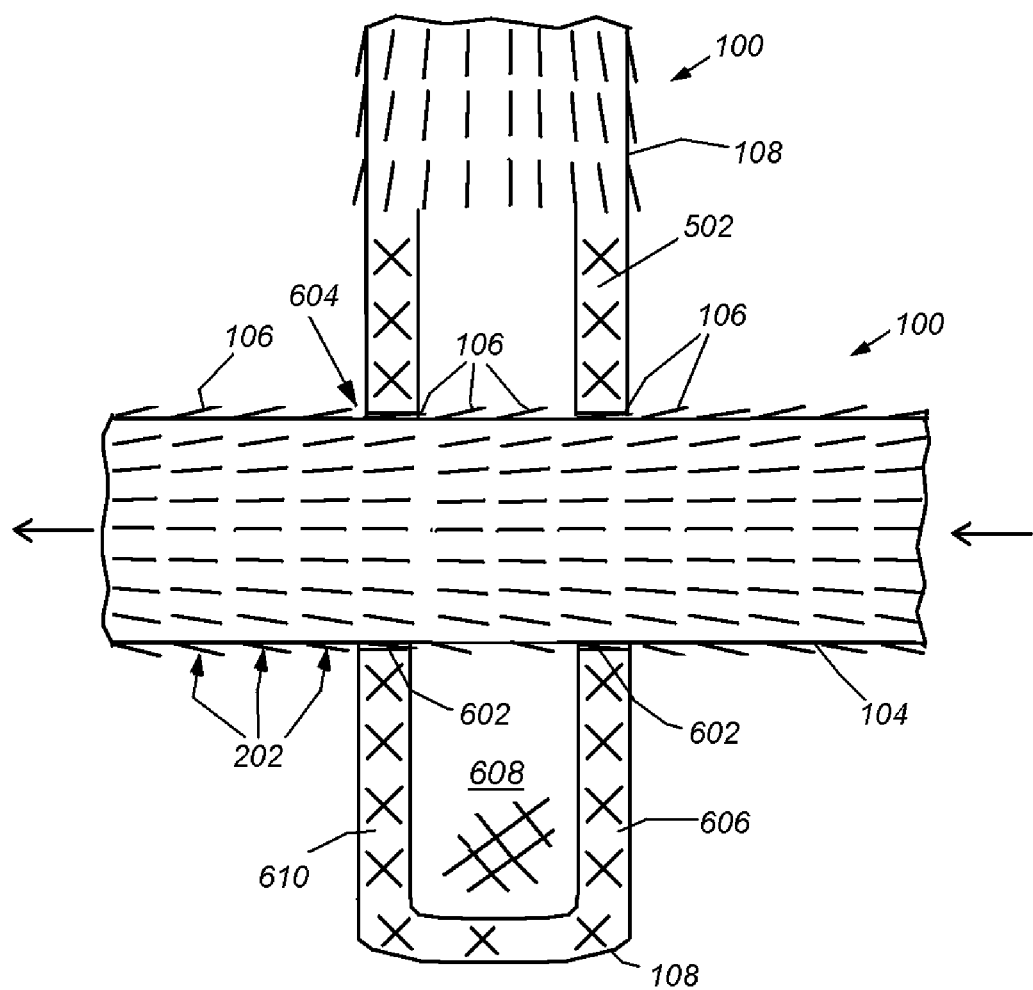
FIG. 6 is a cross-section view along lines 6-6 of FIG. 5 the locking suture needle passing through the terminal end according to the illustrative embodiment.

FIG. 6 is a partial cross-section of the passage of the suture 100 through the braided terminal end 108 along lines 6-6 of FIG. 5. As the suture 100 passes through the terminal end 108, its passage defines a through-path 602. The needle penetrates the first threading wall 606, passes through the hollow center 608 and passes through the second threading wall 608. The force of the needle passage can cause the hollow center 608 to be "pinched" between the walls 606, 608. When the portion of the suture 100 is within the path 602, the barbs flatten against the threading 104 in a "closed" configuration, flattened against the threading. The barbs resume their open configuration when out of the exit 604 of the path 602.

Figure 7:
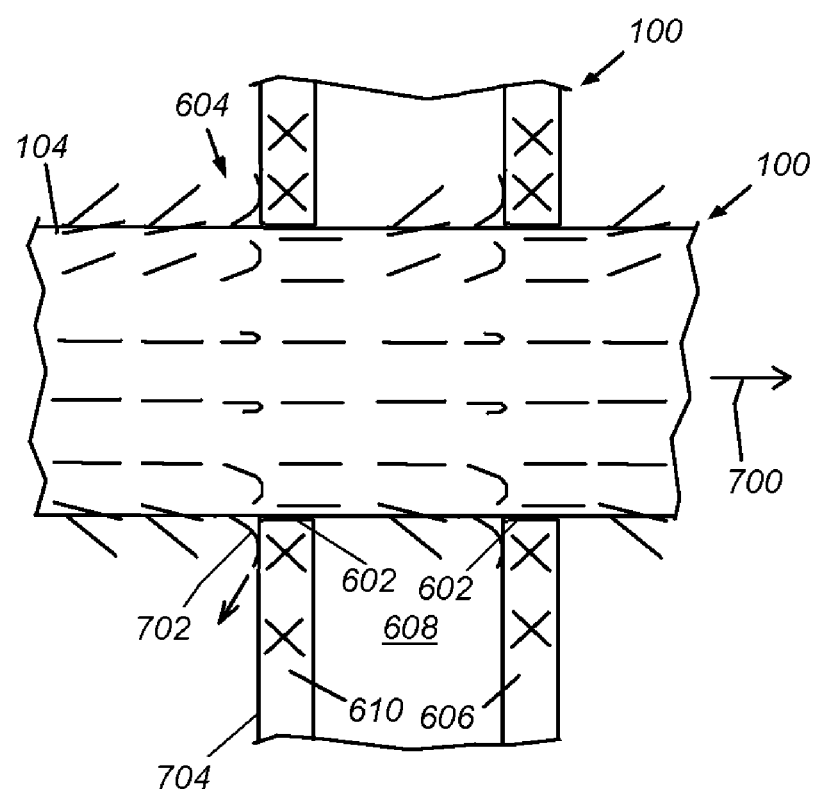
FIG. 7 is a partial close-up view of the cross section of FIG. 6, showing a locking structure created by the splaying of the barbs against the outer surface of the threading according to the illustrative embodiment.

FIG. 7 is a close up view of the exit 604 of path 602 of FIG. 6. When a reverse tension force is applied in the direction 700 towards the terminal end, the barbs 106 that are adjacent to the exit 604 are urged to become splayed 702. The splaying is caused when the barbs 106 in their open configuration are drawn against their bias to the exit 604. The barbs then confront the outer surface 704 of the braided terminal end 108 and roll outwards circumferentially. At this point, the splaying is a locking structure and the suture 100 resists being re-drawn into the path 602. As noted above, further force can cause the threading walls 606, 610 to pinch together and their threading to deform, creating a more secure locking of the barbs to the thread.

Figure 8:
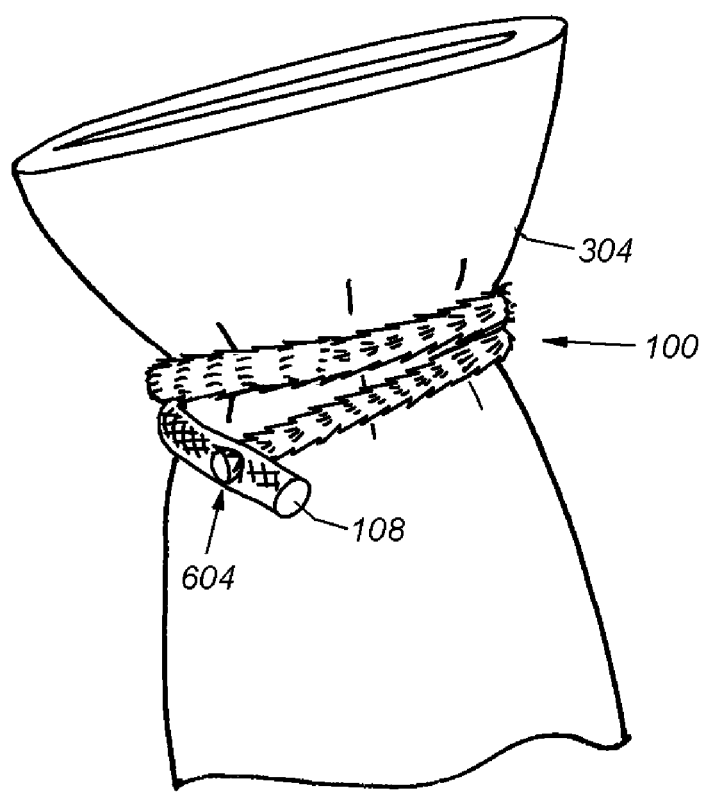
FIG. 8 is a perspective view of a ligation created by a locking suture in place, closing a vessel according to the illustrative embodiment.

To create the lock, the surgeon passes the needle and a portion of the suture 100 through the terminal end 108, as set forth in FIGS. 5-7 above, drawing the rows of barbs through the path 602 until the ligation is tight. When the last barb row is free of the exit, the pulling force is released and the suture rebounds slightly under the internal pressure of the vessel. This causes the last row of barbs to splay against the terminal end and locks the suture without a knot. The surgeon next removes the excess suture thread and needle and proceeds with the procedure as if a knot had been tied. FIG. 8 depicts the final state of the suture 100. A portion of the suture 100 has been drawn through the terminal end 108 and the barbs are splayed against the exit 604. The excess suture has been removed and the clamps are off the vessel 304.

Figure 9:
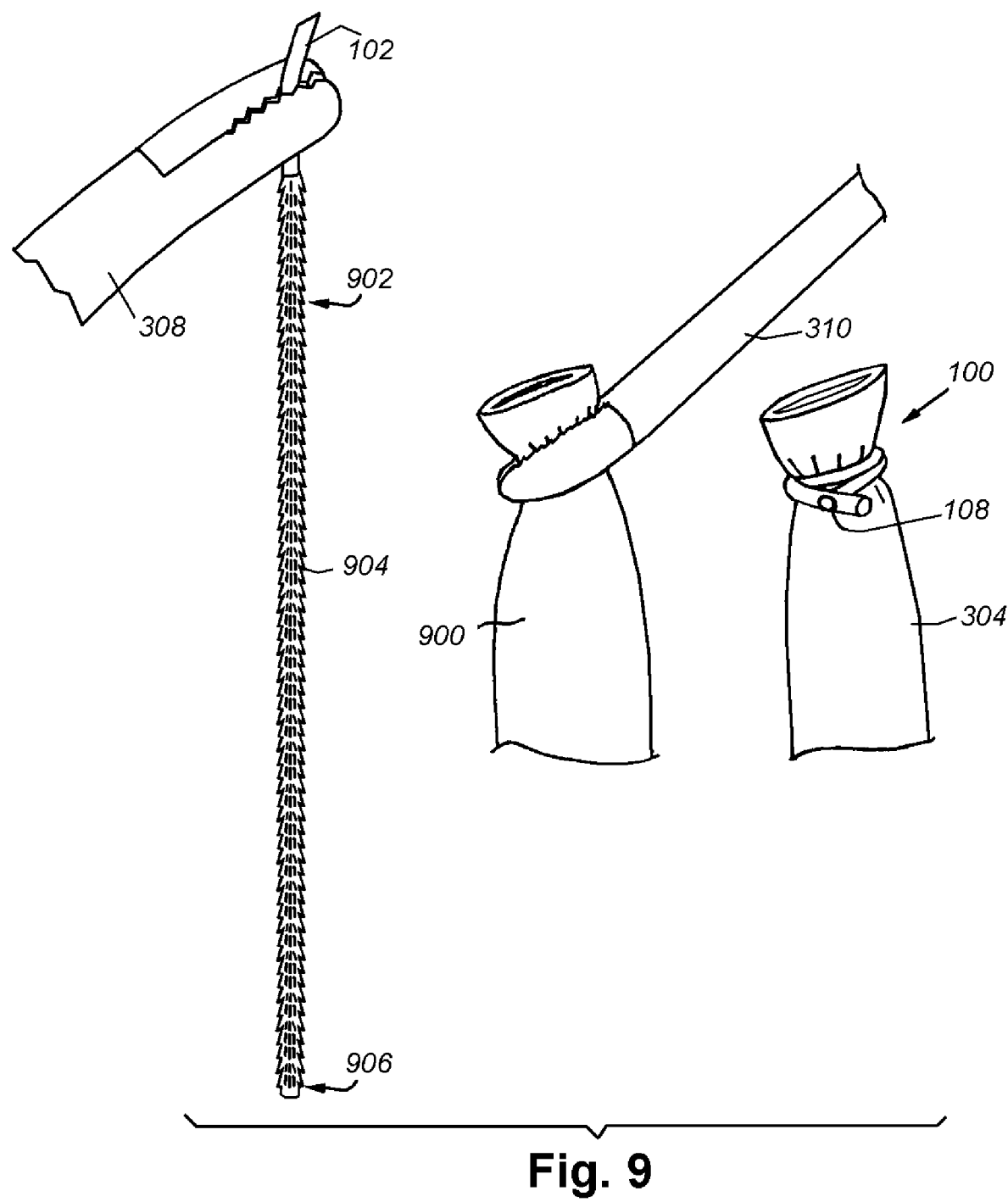
FIG. 9 is a perspective view of a completed ligation and a second vessel to be ligated with the remaining suture according to the illustrative embodiment.
Figure 10:
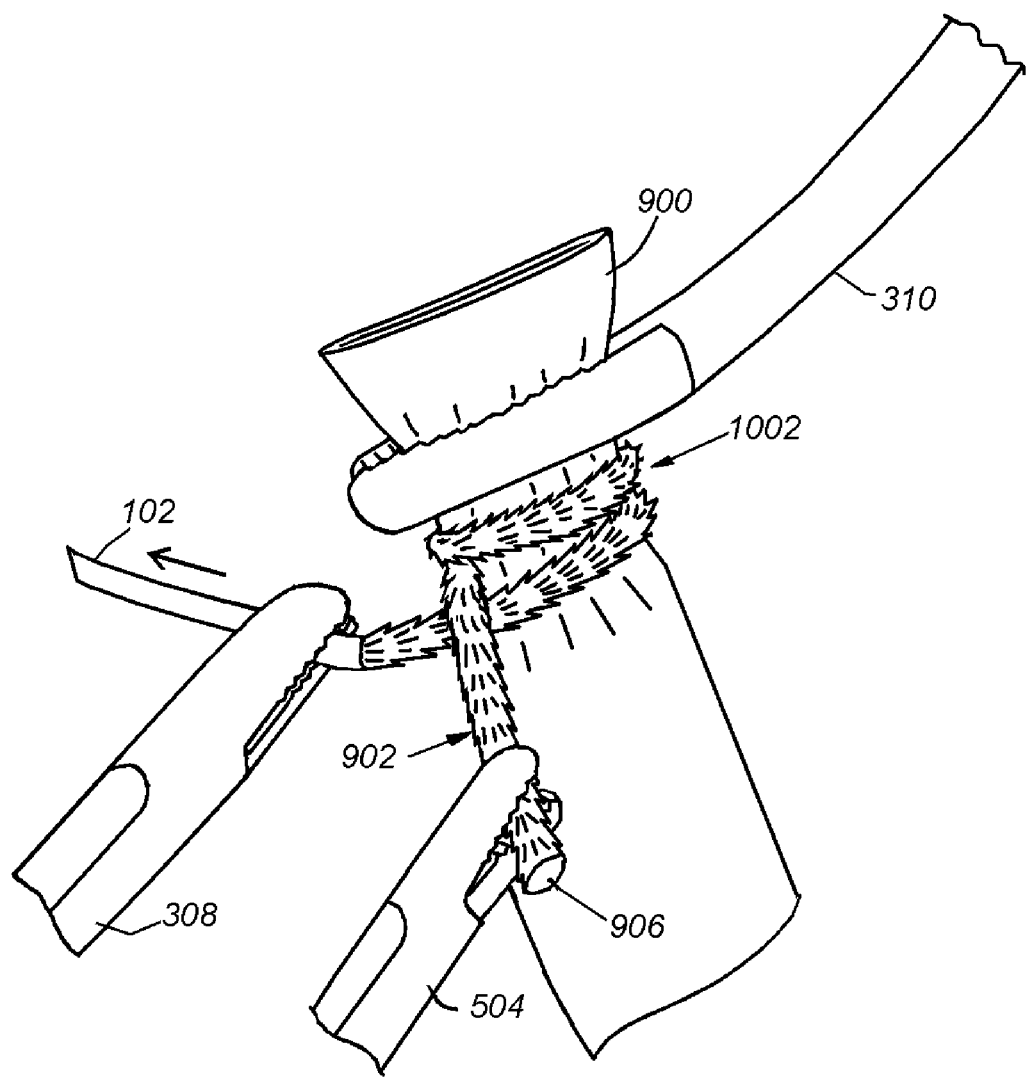
FIG. 10 is a perspective view of a suture needle being driven through the thread of the locking suture according to the illustrative embodiment.

FIGS. 9 and 10 depict the use of the same locking suture 100 to perform a ligation or another closure/suturing task on a second vessel 900 (or other site). FIG. 9 shows the completed ligation on blood vessel 304, as described in FIGS. 3-8 above. A surgeon can be presented with more than one ligation in various procedures, including a testicular ligation and a tubular ligation. The segment of the locking suture 100 that was applied to vessel 304 included the terminal end 108. The remaining portion of the suture 902 comprises the needle 102, segment of thread 904 and a cut end 906. The procedure for applying the ligation follows the steps set forth above. A clamp 310 is used to secure and close the vessel. The surgeon manipulates the suture using a clamping device 308 and wraps the suture around the vessel 900.

FIG. 10 shows the vessel 900 with a of suture wrap 1002. The surgeon is driving the needle 102 through the thread material 902 in the same maneuver as the needle and suture were driven through the braided terminal end, as set forth above. The cut end 906 is held in a clamp 504 and the needle 102 is driven through the thread so that a pulling force can be applied to the thread to pull the thread and barbs through the suture. When the desired tightness is achieved, the pulling force is removed and a tension force is applied in a direction away from the needle that will splay the barbs against the exit and create a locking structure. It is contemplated that given sufficient length of suture thread that two or more ligations can be performed using the same locking suture.

Figure 11:
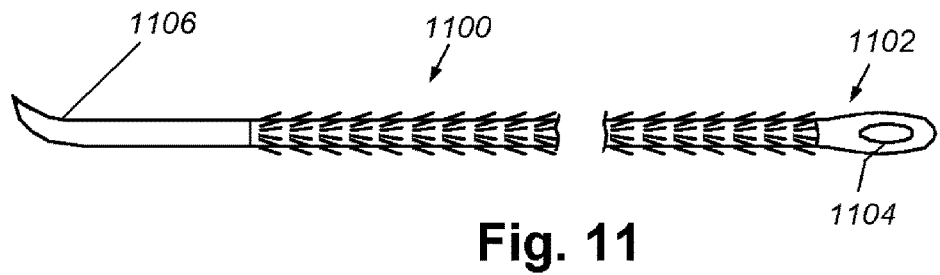
FIG. 11 is a perspective view of a locking suture with a looped terminal end according to a further embodiment.

FIG. 11 is an alternate embodiment that depicts a locking suture 1100 is provided with a terminal end 1102 that defines a loop with a center hole 1104. The center hole 1104 is sized relative to the suture thickness and will allow the needle to pass through the center hole 1104. The surgeon applies the ligation as set forth above, but passes the needle 1106 through the center hole 1104, pulling the thread until the ligation is tight. The barbs create a lock structure (as set forth more fully above) and the excess thread and needle are removed. In the case where one or more additional ligations are called for, the shortened thread is applied as described above, with the needle passing through the thread itself.

Figure 12:
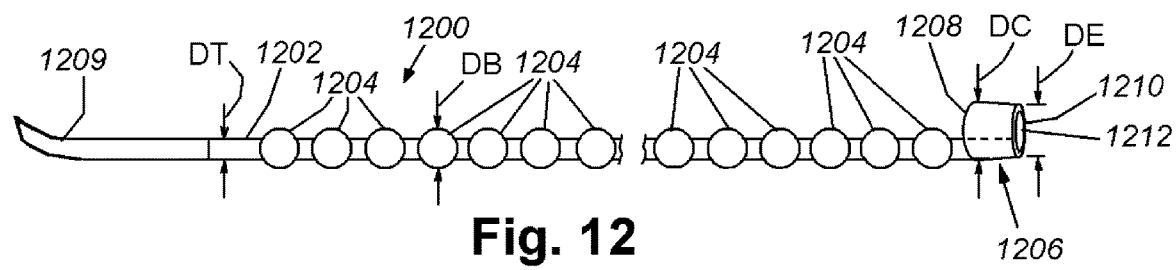
FIG. 12 is a perspective view of a locking suture provided with beading and a collar of the terminal end according to a further embodiment.
Figure 13:
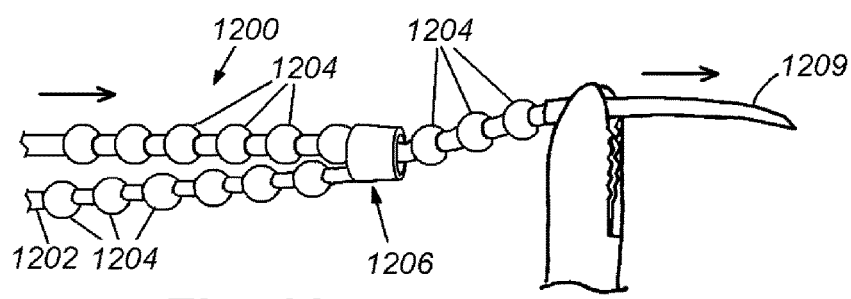
FIG. 13 is a close up view of the locking suture provided with beading being guided through the terminal end collar according to the embodiment.

FIGS. 12-13 show a further embodiment of a locking suture 1200 that has a woven or monofilament thread 1202. With reference to FIG. 12, a plurality of beads 1204 is affixed to the thread 1202 at regular or irregular intervals. The thread can be woven or formed of an elastomeric polymer. The beads can be applied to the thread or formed unitary with the thread. The diameter DB of the beads is greater than the diameter DT of the thread. The terminal end 1206 describes a collar structure that is frustoconical in shape and is constructed and arranged to receive and secure a bead of the beaded threads. The diameter DC collar end 1208 that opens towards the needle 1209 is greater than the diameter DE of the posterior end. The collar is composed of a dissolvable or non-dissolvable elastomeric polymer that expands and rebounds. The posterior center opening 1212 of the collar 1206 is sized so that it can expand to the diameter DB of a bead 1204 and allow passage of a bead 1204 and then rebound to a size that is between the bead diameter DB and the thread diameter DT. This rebound function prevents a bead 1204 from being pulled back through the collar and creates a lock.

FIG. 13 shows a needle 1209 being driven through the collar 1206 and the drawing of beads 1204 as they pass through the collar 1206. This drawing continues until the thread is tight. When the thread is tight and a reverse tension force is applied, the collar diameter prevents the last bead from returning through the collar and a locked structure is formed. This ligature has a single collar and can be used as a locking suture once, unlike the previous embodiments.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein various directional and orientational terms such as "vertical", "horizontal", "up", "down", "bottom", "top", "side", "front", "rear", "left", "right", and the like, are used only as relative conventions and not as absolute orientations with respect to a fixed coordinate system, such as gravity. While the rows of locking barbs are depicted above as extending from the needle to the terminal end, it is expressly contemplated that the barbs can begin further down the suture, at a half way point or another place, such that the suture is part conventional woven thread and part locking barbs. The barbs can be spade-shaped, cylindrical, tubular, spines, rectilinear in shape or another shape. There can be fewer or more barbs than depicted. Successive rows of barbs can alternate in number of barbs and shape of the barbs. The barbs can be arranged at random along the outer surface of the suture thread and without rows. The terminal end can be formed of a unitary elastomeric polymer that provides the passage of the needle and suture as set forth above and resists a reverse force on the barbs, causing them to splay open and lock the suture at the exit. In a further embodiment, a thread material can be an elastomeric polymer and the barbs are a geometric form, such as a spheroid, so that successive spheroids are drawn through a terminal end and form a locking structure against the exit. Accordingly, this description is meant to be taken only by way of example, and not to otherwise limit the scope of this invention.

What is claimed is:

1. A method for creating a ligation without a knot comprising the following steps:
   wrapping a locking suture thread around a vessel;
   driving a needle of the locking suture thread and a first portion of the locking suture thread through a second portion of the locking suture thread;

pulling the first portion of the locking suture thread through the material of the second portion of the locking suture thread, the locking suture thread including a plurality of barbs;

biasing the barbs to lie flat against the first portion of the locking suture thread during the drawing through the second portion of the locking suture thread;

applying a pulling force to the first portion of the locking suture thread for drawing it through the second portion of the locking suture thread until the locking suture thread is tight; and releasing the pulling force so that a reverse tension force being applied to the locking suture thread against a bias of the barbs, the barbs being pulled against their bias splaying outwards against an outer surface of the locking suture thread and an inner surface of the locking suture thread creating a locked structure.

2. The method of claim 1 wherein a remaining portion of the locking suture thread is used to perform a second ligation, the locking suture thread being drawn through the locking suture thread to create a locked structure.

3. The method of claim 1, wherein driving the needle of the locking suture thread and the first portion of the locking suture thread through the second portion of the locking suture thread further comprises grasping the needle with a hemostat, and using the hemostat to drive the needle through the second portion of the locking suture thread.

4. The method of claim 1, wherein the locking suture thread is a hollow woven thread, and wherein driving the needle of the locking suture thread and the first portion of the locking suture thread through the second portion of the locking suture thread further comprises driving the needle of the locking suture thread through a first side of the locking suture thread, through a hollow center of the hollow woven thread, and through a second side of the locking suture thread.

5. The method of claim 1, wherein the locking suture thread is a hollow woven thread, and wherein releasing the pulling force so that the reverse tension force being applied to the locking suture thread against the bias of the barbs further comprises pinching a first side of the locking suture thread against a second side of the locking suture thread and collapsing the hollow woven thread.

6. The method of claim 1 wherein releasing the pulling force so that the reverse tension force being applied to the locking suture thread against the bias of the barbs further comprises collapsing a tube shape of the locking suture thread, thereby providing a greater resistance to the barbs being pulled out back through the thread.

7. The method of claim 6 wherein releasing the pulling force so that the reverse tension force being applied to the locking suture thread against the bias of the barbs further comprises collapsing the tube shape of the locking suture thread and deforming the locking suture thread, thereby providing a greater resistance to the barbs being pulled out back through the thread.

* * * * *